United States Patent
Ligon, Sr. et al.

(10) Patent No.: US 7,096,872 B2
(45) Date of Patent: Aug. 29, 2006

(54) EAR PLUGS AND METHOD OF FORMING SAME

(76) Inventors: James T. Ligon, Sr., 800 S. Main St., Almont, MI (US) 48003; Jeffrey C. Lewis, 26 Rochdale, Rochester Hills, MI (US) 48309

( * ) Notice: Subject to any disclaimer, the term of this patent is extended or adjusted under 35 U.S.C. 154(b) by 208 days.

(21) Appl. No.: 10/256,644

(22) Filed: Sep. 27, 2002

(65) Prior Publication Data

US 2004/0060567 A1 Apr. 1, 2004

(51) Int. Cl.
*A61F 11/00* (2006.01)

(52) U.S. Cl. .................. 128/864; 128/865; 181/135
(58) Field of Classification Search ......... 128/864–868; 181/130, 135
See application file for complete search history.

(56) References Cited

U.S. PATENT DOCUMENTS

| | | | |
|---|---|---|---|
| 3,751,541 A * | 8/1973 | Hegler | 264/508 |
| 3,872,559 A | 3/1975 | Leight | |
| 3,879,505 A * | 4/1975 | Boutillier et al. | 264/48 |
| 3,981,663 A | 9/1976 | Lupke | |
| 4,434,794 A | 3/1984 | Leight | |
| 4,504,206 A | 3/1985 | Lupke et al. | |
| 4,617,849 A | 10/1986 | Ligon | |
| 4,708,624 A | 11/1987 | Ligon | |
| 4,774,938 A | 10/1988 | Leight | |
| 4,789,322 A | 12/1988 | Chan et al. | |
| 5,188,123 A | 2/1993 | Gardner, Jr. | |
| 5,203,352 A | 4/1993 | Gardner, Jr. | |
| 5,573,015 A | 11/1996 | Williams | |
| 5,811,742 A | 9/1998 | Leight | |
| 6,110,404 A | 8/2000 | Ligon, Sr. et al. | |
| 6,398,997 B1 | 6/2002 | Ligon, Sr. et al. | |
| 6,408,981 B1 | 6/2002 | Smith et al. | |
| 6,659,103 B1 * | 12/2003 | Tiemens | 128/864 |
| 2003/0029458 A1 * | 2/2003 | Tiemens | 128/864 |
| 2003/0029460 A1 * | 2/2003 | Tiemens | 128/864 |

FOREIGN PATENT DOCUMENTS

| | | |
|---|---|---|
| EP | 0 707 935 | 4/1996 |
| EP | 1 209 189 | 5/2002 |
| GB | 1 110 287 | 4/1968 |
| WO | WO 01 83187 | 11/2001 |

OTHER PUBLICATIONS

International Search Report dated Jan. 16, 2004. (PCT/US03/28165).
Website at www.envirosafetyproducts.com/html/leight_hearing.htm dated Aug. 19, 2002 (5 pages).
Website at www.eraser.com dated Aug. 23, 2002 (1 page).
Website at www.corma.com/html/products/specs.htm dated Aug. 23, 2002 (1 page).

* cited by examiner

*Primary Examiner*—Michael A. Brown
(74) *Attorney, Agent, or Firm*—Dobrusin & Thennisch PC

(57) ABSTRACT

A process for forming a foamed thermoplastic earplug, comprising the steps of extruding a foamed body of thermoplastic material; shaping the foamed thermoplastic material; and at least partially separating the resulting shaped material for forming individual earplugs.

32 Claims, 1 Drawing Sheet

US 7,096,872 B2

EAR PLUGS AND METHOD OF FORMING SAME

FIELD OF THE INVENTION

The present invention relates to an improved earplug and more particularly to an improved extruded earplug made of a foamed thermoplastic.

BACKGROUND OF THE INVENTION

Earplugs are a common expedient to protect ears and their sensitive structures from excessive noise and from the entry of undesired debris or other matter. Recent designs for earplugs have employed plastics. For example, U.S. Pat. Nos. 4,774,938 and 3,872,559 disclose molded plastic earplugs. Other earplug designs are set forth in U.S. Pat. Nos. 5,811,742; 5,573,015; 5,203,352; 5,188,123; and 4,434,794. Another recent effort to make foamed plastic earplugs is exemplified in U.S. Pat. No. 6,408,981. All of the above-noted patents are hereby expressly incorporated by reference for all purposes.

There remains a need in the art for a low-cost and efficient approach to the manufacture of earplugs, particularly foamed and extruded thermoplastic ear plugs. There is also a need in the art for improved earplug structures for enhancing user comfort, handling and overall earplug performance.

SUMMARY OF INVENTION

The present invention meets the above needs by providing an improved earplug that is made by a process that includes the steps of:

a) extruding a foamed body of thermoplastic material;

b) shaping the thermoplastic material; and c) separating the resulting shaped material for forming individual earplugs.

In a particularly preferred embodiment the earplug is a thermoplastic elastomer material that is waterfoamed, and the foamed body is extruded in the form of a tube.

BRIEF DESCRIPTION OF THE DRAWINGS

Materials and dimensions shown in the drawings are for illustration purposes. They are not intended as limiting. Other materials and dimensions are possible as will be appreciated.

DETAILED DESCRIPTION OF PREFERRED EMBODIMENT

Figure 1A:
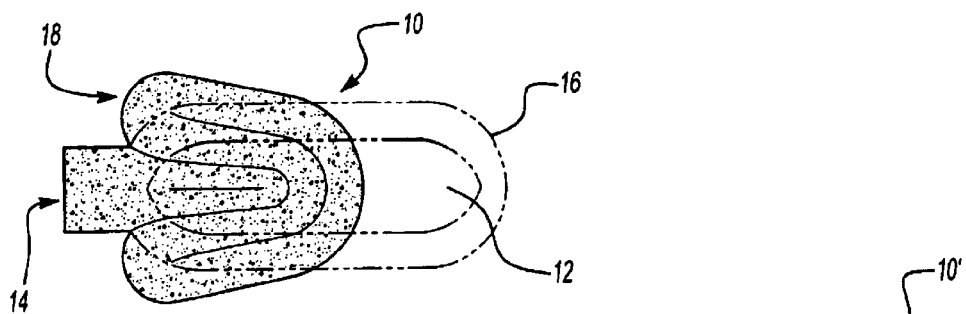
FIGS. 1A and 1B illustrate cross-sectional views of examples of earplugs in accordance with the practice of the present invention.
Figure 1B:
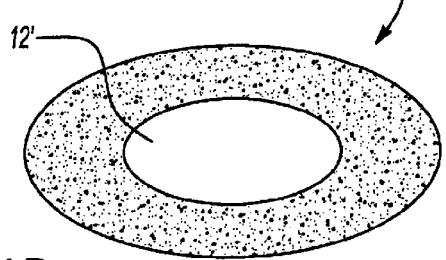

The present invention is predicated upon the discovery of an improved process for the manufacture of an earplug 10 (10'), such as shown in FIGS. 1A and 1B, which process includes the steps of extruding a foamed body of thermoplastic material; shaping (e.g., by plastically deforming a resin) at least a portion of the thermoplastic material; and separating (e.g., by at least partially cutting) the resulting shaped material for forming individual earplugs. In a particularly preferred embodiment the earplug is a thermoplastic elastomer material that is waterfoamed.

As will be appreciated from the discussion that follows, one of the unique aspects of the present invention is that novel earplug structures may be produced using a foamed plastic, and particularly from an extruded foam tube of a thermoplastic material. For example, the present invention may be used to make solid core earplugs. However, as seen in FIGS. 1A and 1B, one unique structure for an earplug 10 is prepared from the extrusion of a tubular profile, and includes a hollow core 12 (12'). In addition, processing according to the present invention allows for the formation of a skin over substantially the entirety of the outer surface of the earplug. Referring to FIG. 1A, the earplug 10 may also include a stem portion 14, that adjoins an initially bulbous portion 16 (the latter shown in phantom to depict its initial state and including the hollow core 12). The thickness and structure of the walls defining the respective portions are such that hinge points are formed where the portions adjoin. In this manner, the stem can be used as a gripping surface for inserting the earplug 10 into an ear. The bulbous portion 16 will deform (as illustrated by the phantom lines), and effectively collapse upon itself, forming a mushroom-like head 18 about the stem. The resulting collapsed structure can then be maintained within an ear canal. It will be appreciated in all embodiments that ear canal retention may also be enhanced by expansion of a compressed foam after placement in the ear canal.

A preferred approach is to foam the earplugs while they are being extruded, while they are being shaped or both. In a particularly preferred embodiment, the earplugs are foamed using a waterfoam technique, by the liberation of gas from water that is mixed with the feed material prior to extrusion. By way of example, the teachings of U.S. Pat. Nos. 6,398,997 and 6,110,404, hereby incorporated by reference, illustrate one preferred approach for waterfoaming. Those patents teach a method for extruding foam of a plastic resin material, such as a thermoplastic elastomer (which is used herein, without limitation, for illustration purposes), which includes the steps of mixing the resin (e.g., thermoplastic elastomer) with water, introducing the mix to an extruder, melting and compressing the resin (e.g., thermoplastic elastomer) and water and extruding the resultant mix as foam. In more detail, a first quantity of resin (e.g., thermoplastic elastomer) in pellet form is mixed with a second quantity of water, and optionally soaked for a predetermined period of time after mixing. It will be appreciated that pursuant to this technique, superheated water within the resin (e.g., thermoplastic elastomer) is in a generally liquid state, owing to the high pressures encountered in the extruder die. When the resin leaves the die and the pressure upon is reduced (e.g., to atmospheric), a resulting effect of the pressure reduction is to flash the liquid to a gaseous state, thereby forming pores within molten or semi-molten plastic. As the pores and plastic grow, if unconstrained, the volume of the foam increases and the density decreases. A layer of densified or unfoamed plastic, effectively a skin, may be formed on an outer surface of the foam, for example, by being cooled for solidifying before the foam expands on the outer surface.

Figure 2:
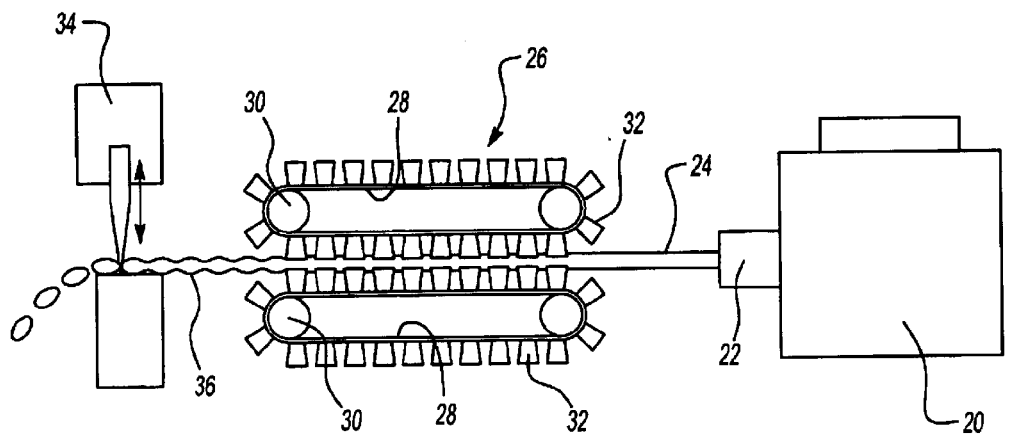
FIG. 2 illustrates a schematic of a production line for extruding and shaping an ear plug according to the present invention.

As seen in FIG. 2, the mixed water and thermoplastic elastomer is introduced to an extruder 20. The thermoplastic elastomer is melted, compressed, and mixed with the water to a uniform mix of thermoplastic elastomer and water. The mix is extruded through a die 22 of the desired shape, wherein the water expands in a vapor form to create foam cells (which may be open cell, closed cell or a combination thereof) with the cells having walls of the thermoplastic elastomer, thereby forming an at least partially foamed extrusion 24. A skin optionally may be formed over the some or all of the exterior of the extrusion at this point. In another embodiment, water retention is enhanced by exposing a first quantity of the thermoplastic elastomer in pellet form to steam to increase an amount of water retained by the thermoplastic elastomer. For example, the amount of retained water is preferably in a range of between approximately 3% to 6.75%. Other foaming techniques may also be employed as desired, such as the use of an art-disclosed chemical blowing agent.

Preferably, upon exiting a die 22 of the extruder 20, the extrusion 24 will be a substantially completely foamed material, although it may only be partially foamed. After exiting the die 22, the extrusion is shaped as desired.

The step of shaping may be done in any suitable manner. For example, it is possible to have opposing surfaces, one or both of which are shaped to a desired configuration, contacting the extrusion for plastically deforming it, (e.g., while the temperature of the extrusion is still at or near the melting point of the extrusion material. In a preferred embodiment, shaping is performed nearly simultaneously about substantially the entirety of the periphery of the extrusion 24. A particularly preferred approach to shaping is by deformation of the extrusion in accordance with a suitable method, such as those disclosed in U.S. Pat. Nos. 4,789,322; 4,504,206; and 3,981,663; hereby expressly incorporated by reference. An example of a suitable machine for use in the present invention is commercially available from Corma, Inc., such as under the Model numbers VO52. Preferably, the machine will have a line speed of at least about 1 meter per minute, more preferably at least about 5 meters/minute, and still more preferably at least about 12 meters/minute and even still more preferably at least about 20 meters/minute. In this manner, it is contemplated that amounts of products ranging from about 5 to about 30 kg/hour or higher, and more preferably about 15 to about 25 kg/hour are possible.

Figure 3:
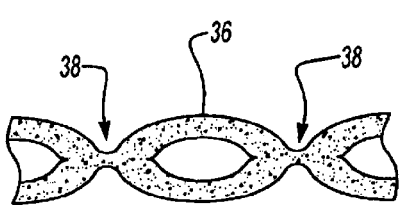
FIG. 3 illustrates a sectional view of an earplug precursor.

In general, as seen for example in FIG. 2, it is contemplated that a suitable shaping machine 26 will include opposing webs 28, chains or the like that rotate about a sprocket or other suitable roller 30 and which each include a plurality of successive traveling mold portions 32 (which optionally may be heated, be removable, be interchangeable with other mold portions, or contain a sharp edge for cutting). Upon placing an extrusion between the mold portions 32 (e.g., aligning it with a suitable guide device or in a channel disposed between the mold portions) the webs 28 are synchronously advanced for feeding the extrusion through the opposing mold portions 32, whereupon the extrusions are shaped to the desired shape (corresponding to the shape of the mold portions) for an ear plug, and may optionally be cut, such as with a blade associated with a suitable cutter 34. A preferred approach is to form a cavity within the mold portions that substantially approximates the shape of the resulting desired earplug. Thus, as seen in FIG. 3, an earplug precursor 36 is effectively formed upon passage of the extrusion 24 through the shaping machine 26, which corresponds in size and shape with the respective mold portions of the shaping machine. Optionally, mold portions may be fitted with suitable vacuum lines for aid in forming the earplugs, fluid lines (e.g., air or water) for temperature control of the product as it is being shaped, or a combination thereof. It will further be appreciated that controlled cooling of an extrusion could have the effect of forming a skin, which in turn, could help impart rigidity to the part so that it is strong enough for subsequent handling, without undesired deformation.

The shaping machine may be located immediately adjacent an extrusion die or spaced apart from it. Thus, it is possible that some foaming may occur during shaping. In this manner, it is possible that the temperature of the extrusion may be controlled during the shaping by heating or cooling it along the line. Other like continuously fed shaping machines and techniques may also be employed and the present invention is therefore not limited solely to the above embodiment.

As described previously, individual earplugs are formed upon the separation of the extrusion into segments. Thus, before, during or after shaping, the earplug precursors are at least partially cut at their respective end portions 38. The cutting may be performed with any suitable tool. For example, the edges of the mold portions 32 may be adapted for cutting or for closing the ends of each earplug precursor. A blade may be associated with the extruder upstream or downstream of the shaping machine. An example of a suitable cutting machine for use in the present invention is a commercially available puller/cutter from The Harrel Company (e.g., one that employs one or a combination of a machine under the designations of ROLLERPULLER or NOCLUTCH CUTTER). Another alternative would be to employ a suitable die cutting machine (e.g., a rotary die cut machine, such as is available from Delta Industrial). The cutting machine may optionally employ a suitable sensor (e.g., an optical sensor) to sense to location of a predetermined feature of a workpiece for triggering the cutter to cut the workpiece.

Other processing steps may also be employed as desired. For example, during extrusion, during shaping or both, the extrusion 24 or earplug precursors 36 may be stretched, cut with a hot blade, or both for forming a skin on one or both ends of the earplug. Examples of suitable stretch-cutting techniques that may be employed are disclosed in U.S. Pat. No. 4,708,624 and U.S. Pat. No. 4,617,849, hereby incorporated by reference. Thus, the extrusion 24 or earplug precursors 36 may be stretched longitudinally and cut transversely while stretched. It is also possible that flash will be generated during processing, and the present invention also contemplates that a step be employed for flash removal, in instances when control over processing and equipment cannot avoid the formation of flash in the first instance.

Figure 4:
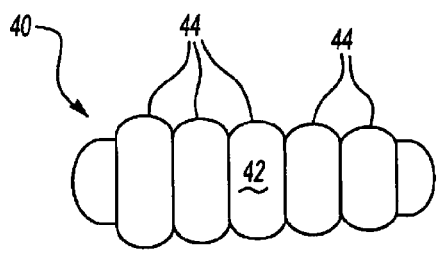
FIG. 4 illustrates an alternative configuration of an earplug according to the present invention.

The outer surface of an earplug in accordance with the present invention may exhibit any suitable surface texture, contour or combination thereof. It may include a smooth surface as illustrated in the above embodiments. Alternatively, as seen in FIG. 4, an earplug 40 may include a corrugated outer surface 42 or otherwise shaped effectively for forming one or a plurality of longitudinally disposed sealing rings 44. Though shown for illustration purposes as being generally egg-shaped, such earplug 40 may have any other suitable shape.

The extrusion or earplug precursors may be coated over some or all of their bodies with a suitable coating, such as a tackifier, a powder, a reduced friction material, a medicament (e.g., a fungicide, a bactericide, or another medicine), an antiseptic, or combinations thereof. They may have a design or text printed on a surface (e.g., screen printed, laser printed, hot stamped or the like). Though smaller earplugs are also possible in accordance with the present invention, preferably the earplugs are at least about 25 mm in length.

In one highly preferred embodiment, though not a necessary requirement to fall within the scope of the present invention, a preferred foamed earplug is believed to be capable of exhibiting a mean attenuation level (in accordance with ANSI S3.19-1974) of at least about 10 dB, and more preferably at least about 20 dB within a frequency range of about 125 to about 250 Hz; and at least about 20 db, and more preferably at least about 35 db for frequencies greater than about 500 Hz. A highly preferred ear plug in accordance with the present invention is believed to exhibit an NRR mean attenuation level of at least about 40 db at a frequency of about 3000 Hz. Thus, though again not a necessary requirement to fall within the scope of the present invention, preferred earplugs in accordance with the present invention are believed to and preferably will exhibit a Noise Reduction Rating (NRR) of at least about 5, more preferably at least about 15, and still more preferably at least about 20; and in one preferred embodiment, the earplugs may have a NRR of between about 15 and 40, and more preferably between about 20 and 35.

The material selected has a density sufficient to produce earplugs having densities ranging from about 12 to 31 pcf (about 0.2 to 0.5 g/cc), or more preferably, within a range of from about 20 to 25 pcf (about 0.3 to 0.4 g/cc). In addition, in one preferred embodiment, the material of the earplug (in an unfoamed state) would exhibit a Shore A durometer hardness of between about 60 and about 80.

Foamed materials herein may be an open or closed cell material. In one preferred embodiment, at least about 50% by volume, more preferably at least about 65% by volume of the overall cell volume will include closed cells. The foamed materials of the earplugs may be skinned or unskinned. They may have a continuous or uniform density throughout, or a density gradient. Preferably the material employed will be sufficiently pliable and elastic that a user will be able to compress the material for insertion into an ear and the earplug once inserted will expand, so that the earplug will be retained in the ear. Thus, generally it will be appreciated that the material of the earplug will exhibit a relatively low compression set and a relatively low load/deflection.

Preferred materials for forming the earplugs are low density thermoplastic elastomeric materials such as thermoplastic polyolefins/ethylene-propylene (PEP OR EPDM), thermoplastic block copolymers/styrene-butadiene (SBS) and styrene-isoprene (SIS), thermoplastic polyester, thermoplastic polyurethane (PU)/polyester/polyether, thermoplastic vulcanizates (e.g., comprising blends of cured olefin rubber and thermoplastic olefin resin), poly (vinyl ester) (e.g., chemically blown), melt processable rubbers, polyamide blocks, thermoplastic rubber, and viscoelastic polyurethane. Santoprene® thermoplastic rubber (e.g., such as that sold by Advanced Elastomer Systems under the designation 123-52W242 or X123-48W242) may also be used. Other thermoplastic foams may alternatively be employed. Blends of the above materials likewise may be employed.

In one embodiment where a low friction surface is desired, the ear plugs are coated over at least a portion of their external surfaces with a low friction coating, which may take the form of a powder, wax, an oil, or even a polymer (such as a fluoropolymer, a high-density polyolefin (e.g., HDPE), a silicon-containing compound (e.g., an organosilane) or the like. The coating may be emulsified or dispersed in a liquid to facilitate the coating step. Alternatively, for example, when a polymer coating is employed it is possible that it is coextruded with the foamed thermoplastic. Other suitable coating techniques may be employed such as dipping, brushing, curtain coating, spraying, swabbing, or the like. Other organic or inorganic coatings may also be employed. Additives or reinforcements may also be incorporated into or on the surface of the earplug, such as colorants, stabilizers, fillers, or other art-disclosed additives.

Earplugs prepared in accordance with the present invention may be packaged at a point of manufacture (e.g., at a manufacturing plant) or at a packaging site that is remote from the point of manufacture (e.g., at a wholesale or retail distribution outlet). One embodiment of the present invention thus contemplates the production of a plurality of earplugs that facilitate the shipment or transport of the earplugs from the point of manufacture to the point of distribution. Accordingly, in this embodiment, the earplugs (e.g., at least partially joined at their ends) are extruded to form a continuous length of straight or coiled material (e.g., coiled about a core), which can subsequently be cut into individual earplugs or into pairs of earplugs (e.g., with a partial cut allowing for ready detachment of a pair into individual earplugs) that can be separated from each other by the end user. Suitable handling equipment may be employed during these operations, such as a stacked cooling conveyor to permit for cooling without uncontrolled plastic deformation. At the end of the conveyor, the extrusion could be placed on a core and coiled.

The earplugs manufactured in accordance with the present invention can be provided alone or in combination with other items, as part of a kit. For example, it may be possible that a kit would include ear plugs of the present invention along with an eye covering (e.g., glasses, goggles, blinders, or the like), one or more toiletries for personal hygiene, a head covering, a carrying case, a breather, a face mask, a protective body suit, a safety hat, steel-toed boots, a strap for connecting the ear plugs into a single assembly, a light, a reflective safety garment, or a combination of at least two of such items.

Thus, it is possible within the present invention that the ear plugs herein are provided for use by a construction worker, a musician, a concert-goer, a firearm range user, an air transport passenger, heavy tool equipment operators, persons who work in a factory, automobile or boat racers or race spectators, airfield workers, or the like.

The methods taught herein are not limited to the manufacture solely of earplugs, but could be extended to the manufacture of other foamed thermoplastic articles, such as (without limitation) caps, plugs, covers, feet, clips, hangers (e.g., for a wiring harness or fluid lines) fasteners, tubing retainers, or other parts (particularly parts in which a hollow core is desired) that can be molded from an extruded profile, by moving dies or other mold portions downstream from the extruder die.

The present invention also contemplates the performance of the methods herein for the manufacture of shaped co-extruded articles. Accordingly, in one embodiment, a coextrusion is shaped in an operation downstream from the extrusion die.

Dimensions and materials identified in the attached Figures are for illustration purposes and may vary depending upon the intended application in accordance with the teachings of the present invention. The present invention is not intended to be limited to the specific features of the Figures even though the invention encompasses the same.

The illustrative embodiments set forth in the above constitute examples of the principles of the present invention. Numerous alternatives will readily occur to the person skilled in the art, without departing from the scope of the present invention as set forth in the following claims.

What is claimed is:

1. A process for forming a foamed thermoplastic article, comprising the steps of:
   a) extruding a foamed tubular body of thermoplastic material;
   b) feeding the extruded tubular body of thermoplastic material through a plurality of successive opposing traveling mold portions;
   c) shaping the foamed thermoplastic material in the mold portions for forming ear-plug precursors; and
   d) at least partially separating the resulting shaped material for forming ear plugs.

2. The process of claim 1, wherein the extrusion step includes a waterfoaming step.

3. The process of claim 1, wherein the thermoplastic material is a thermoplastic elastomer.

4. The process of claim 1, wherein the step of separating includes forming only a partial cut in the resulting shaped material.

5. The process of claim 1, wherein the resulting article includes a corrugated outer surface.

6. The process of claim 5 wherein the resulting earplug is generally egg-shaped.

7. The process of claim 1, wherein the foamed body is tubular.

8. The process of claim 7, wherein the resulting article includes a hollow core.

9. The process of claim 1, wherein the resulting article is an earplug that includes a stem portion and a bulbous portion that is collapsible upon itself.

10. The process of claim 1 further comprising printing a design or text on a surface on the earplug precursors.

11. The process of claim 1 further comprising the step of co-extruding a polymer coating on the thermoplastic.

12. The process of claim 1 wherein the step (d) includes steps of forming a continuous length of material, partially cutting the length of material for subsequent separation into individual earplugs by an end user.

13. A process for forming a foamed thermoplastic earplug, comprising the steps of:
   a) mixing water and a thermoplastic material to form a mix;
   b) introducing the mix to an extruder;
   c) extruding a foamed body of thermoplastic material;
   d) plastically deforming the foamed thermoplastic material; and
   e) at least partially separating the foamed body of thermoplastic material for forming individual earplugs.

14. The process of claim 13, wherein the thermoplastic material is a thermoplastic elastomer.

15. The process of claim 13, further comprising coating the resulting earplug over at least part of its exterior surface.

16. The process of claim 15, wherein the coating is selected from a tackifier, a powder, a reduced friction material, a medicament, an antiseptic or combinations thereof.

17. The process of claim 13, wherein the resulting earplug includes a corrugated outer surface configured for defining at least one sealing ring.

18. The process of claim 13, wherein the foamed body is tubular.

19. The process of claim 18, wherein the resulting earplug includes a hollow core.

20. The process of claim 13, wherein the resulting earplug includes a stem portion integrated with a bulbous portion that is collapsible upon itself about hinge points.

21. An earplug made according to the process of claim 20.

22. The process of claim 13 wherein the resulting earplug as a density from about 12 to 31 pcf (about 0.2 to 0.5 g/cc).

23. A process for forming a foamed thermoplastic earplug, comprising the steps of:
   a) waterfoam extruding a tube of a thermoplastic elastomer material;
   b) feeding the extruded thermoplastic elastomer material through a plurality of successive opposing traveling mold portions;
   c) plastically deforming the tube of foamed thermoplastic elastomer material to form a series of adjoining earplug precursors each having a hollow core; and
   d) separating the resulting earplug precursors for forming individual earplugs.

24. The process of claim 23, wherein the resulting earplug includes a corrugated outer surface adapted for defining a plurality of sealing rings.

25. The process of claim 23, wherein the resulting earplug includes a stem portion integrated with a bulbous portion that is collapsible upon itself about hinge points.

26. An earplug made according to the process of claim 23.

27. The process of claim 23, wherein the separating step includes stretch cutting.

28. A process for forming a foamed thermoplastic elastomer earplug, comprising the steps of:
   a) providing a thermoplastic elastomer resin having a shore A durometer hardness of between about 60 and about 80;
   b) extruding through an extrusion die the mixture of water and thermoplastic elastomer resin to form at least a partially foamed extrusion;
   c) after it exits the die, feeding the extrusion through a plurality of successive opposing traveling mold portions that circulate about a roller at a line speed of at least about 1 meter per minute;
   d) shaping the extrusion into the desired shape for an earplug having a hollow core corresponding with the shape of the mold portions; and
   e) at least partially cutting the extrusion, wherein the foam in resulting ear plugs has a density of about 12 to 31 pcf and includes at least about 50% by volume of closed cells.

29. The process of claim 28 wherein the resulting shape includes a corrugated outer surface.

30. The process of claim 28 wherein the shaping step (d) occurs while the resin is still at an elevated temperature from the extruding step (b).

31. The process of claim 28 further comprising providing the resulting earplugs as part of a kit that includes an eye covering, one or more toiletries for personal hygiene, a head covering, a carrying vase, a breather, a face mask, a protective body suit, a safety hat, steel-toed boots, a strap for connecting the earplugs into a single assembly, a light, a reflective safety garment, or a combination of at least two of such items.

32. The process of claim 28 wherein a shaping machine spaced apart from the extrusion die houses the traveling mold portions.

* * * * *